US006413930B1

(12) United States Patent
Ratti et al.

(10) Patent No.: US 6,413,930 B1
(45) Date of Patent: Jul. 2, 2002

(54) USE OF CCK-B RECEPTOR ANTAGONISTS FOR THE TREATMENT OF SLEEP DISORDERS

(75) Inventors: Emiliangelo Ratti; David Gordon Trist; Giovanni Gaviraghi; Francesco Crespi; Angelo Mario Reggiani, all of Verona (IT)

(73) Assignee: Glaxo Wellcome Spa, Verona (IT)

( * ) Notice: Subject to any disclaimer, the term of this patent is extended or adjusted under 35 U.S.C. 154(b) by 0 days.

(21) Appl. No.: 08/809,734

(22) PCT Filed: Oct. 12, 1995

(86) PCT No.: PCT/EP95/04024

§ 371 (c)(1),
(2), (4) Date: Apr. 10, 1997

(87) PCT Pub. No.: WO96/11689

PCT Pub. Date: Apr. 25, 1996

(30) Foreign Application Priority Data

| Oct. 14, 1994 | (GB) | 9420703 |
| Oct. 14, 1994 | (GB) | 9420704 |
| Nov. 16, 1994 | (GB) | 9423098 |

(51) Int. Cl.$^7$ .................................................. A61K 38/00
(52) U.S. Cl. .......................................... 514/2; 514/219
(58) Field of Search ...................................... 514/219, 2

(56) References Cited

U.S. PATENT DOCUMENTS 4,950,664 A * 8/1990 Goldberg .................... 514/219

FOREIGN PATENT DOCUMENTS

| EP | 0 558 104 | 9/1993 |
| WO | 93 15059 | 8/1993 |

OTHER PUBLICATIONS

Mosconi et al., *Int. J. Clin. Pharmacol. Res.*, 1993, 13/6 (331–334).
Nishida et al., *J. Pharmacol. Exp. Ther.*, 1994, 269/2 (725–731).
Makovec, *Drugs Future*, 1993, 18/10 (919–931).

* cited by examiner

Primary Examiner—Zohreh Fay

(57) ABSTRACT

The use of CCK-B antagonists for the treatment of sleep disorders.

12 Claims, No Drawings

USE OF CCK-B RECEPTOR ANTAGONISTS FOR THE TREATMENT OF SLEEP DISORDERS

This application is a 371 of PCT/EP 95/04024 filed on Oct. 12, 1995.

The present invention relates to the use of CCK-B antagonists for the treatment of sleep disorders.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxyl terminal octapeptide, CCK-8 (also a naturally occurring neuropeptide), and 39- and 12-amino acid forms. Gastrin occurs in 34-, 17- and 14- amino acid forms, with the minimum active sequence being the C-terminal tetrapeptide, Trp-Met-Asp-Phe-$NH_2$ (CCK-4) which is the common structural element shared by both CCK and gastrin.

CCK and gastrin are gastrointestinal hormones and neurotransmitters in the neural and peripheral systems and perform their respective biological roles by binding to particular receptors located at various sites throughout the body. There are at least two subtypes of cholecystokinin receptors termed CCK-A and CCK-B and both are found in the periphery and in the central nervous system.

The CCK-A receptor, commonly referred to as the "peripheral-type" receptor, is primarily found in the pancreas, gallbladder, ileum, pyloric sphincter and on vagal afferent nerve fibers. Type-A CCK receptors are also found in the brain in discrete regions and serve to provide a number of CNS effects. Due to the ability of CCK-8 and Type-A CCK-selective agonists to suppress food intake in several animal species, considerable interest has been generated toward the development of new substances which function as Type-A receptor-selective CCK agonists in order to serve as anorectic agents.

The CCK-B or gastrin receptors are found in peripheral neurons, gastrointestinal smooth muscle and gastrointestinal mucosa, most notably in parietal cells, ECL cells, D cells and chief cells. CCK-B receptors also predominate in the brain and have been implicated in the regulation of anxiety, arousal and the action of neuroleptic agents.

Sleep disorders are the disturbances of sleep that affect the ability to fall and or stay asleep, which involve sleeping too much or result in abnormal behaviour associated with sleep. There are two types of sleep which cyclical and are marked by characteristic electro-encephalograms (EEG) and other changes including eye movements. The first phase of sleep which in normal sleep accounts for 75–80% of total sleep time is referred to as the non-rapid-eye-movement (NREM) type and this is characterised by slow waves on the EEG. The second sleep type (REM-rapid eye movement) which follows NREM is characterised by EEG low voltage fast activity and occurs 5 to 6 times during a normal nights sleep. In sleep disorders the balance of the two types of sleep is disturbed.

We have now found compounds which exhibit an antagonist activity at the CCK-B receptor influence sleep patterns and are therefore useful for the treatment of sleep disorders.

Thus the present invention provides for the use of a compound having an antagonist activity at the CCK-B receptor in the manufacture of a medicament for the treatment of sleep disorders.

Examples of suitable CCK-B antagonists for use in the treatment of sleep disorders includes the 1,4-benzodiazepine derivatives having CCK-B antagonist activity described in EPA 167919, EPA 284256, EPA 434360. EPA 434364, EPA 434369, EPA 514125, EPA 51426, EPA 514133, EPA 508796, EPA 508797, EPA 508798, EPA 508799, EPA 523845, EPA 523846, EPA 559170, EPA 549039, WO 9211246, WO 93032078, WO 9308175, WO 9307131, WO 9317011, WO 9319053, WO 9308175. WO 9413648 WO 9403437. The subject matter of the above identified published patent applications are incorporated herein by reference. Within the 1,4 benzodiazepine derivative disclosed above a particularly useful class of CCK-B antagonists include representated by the general formula (I).

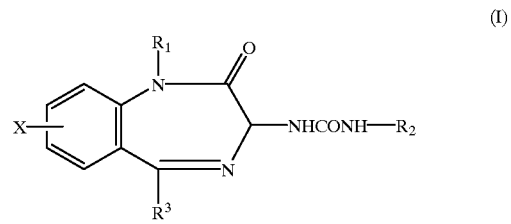

(I)

and N-oxides thereof and pharmaceutically acceptable salts thereof wherein $R_1$ represents $C_{1-6}$ alkyl (optionally substituted by hydroxyl $C_{1-4}$ alkoxy, $COR_4$, $CONR_5R_6$ or $C_{3-7}$ cycloalkyl) or $C_{3-7}$ cycloalkyl;

$R_4$ represents $C_{1-6}$ alkoxy or optionally substituted phenyl;

$R_6$ is methyl or ethyl and $R_6$ is phenyl or $R_5$ and $R_6$ together form a $C_4$–$C_6$ alkylene chain, which may be substitued by 1 or 2 alkyl groups;

$R_2$ represents a substituted or unsubstituted phenyl group (wherein the substitutents may be 1 or 2 of halo, $C_{1-4}$ alkyl, nitro, cyano, trifluoromethyl, trifluoromethoxy, $C_{1-4}$alkylthio or $(CH_2)n\,R_7$ wherein $R_7$ is hydroxy, $C_{1-4}$ alkoxy, $CO_2R_8$, $NR_8R_9$, $SO_2NR_8COR_{10}$, $CONR_8SO_2R_{10}$, or $R_7$ represents a tetrazolyl, carboxamidotetrazolyl, 3-trifluoromethyl-1,2-4-triazolyl or 5-oxo-1,2,4 oxadiazolyl group, which groups may be substituted on one of the nitrogen atoms by a $C_{1-4}$alkyl group;

$R_8$ represents hydrogen of a $C_{1-4}$alkyl group;

$R_9$ independently represents hydrogen or a $C_{1-4}$alkyl group or the group $SO_2CF_3$;

$R_{10}$ represents $C_{1-4}$alkyl;

$R_3$ represents $C_{1-6}$ alkyl $C_{3-7}$ cycloalkyl, phenyl (optionally substituted by halogen), azacycloalkyl or alkyl substituted by an amino, $C_{1-4}$ alkylamino, di$C_{1-4}$alkylamino, morpholino, pyrrolidino, piperidino, hexamethylene, thiomorpholino or N-methyl piperazino group; X represents hydrogen or halogen.

Within this class particularly preferred compounds include those wherein $R_1$ is alkyl e.g. methyl, isopropyl or $CH_2COR_4$ wherein $R^4$ is optionally substituted phenyl or the group $CH_2CO\ NR_5R_6$ wherein $R_5$ is methyl or ethyl and $R_6$ is an optionally substituted phenyl group or $NR_5R_6$ represents a pyrrolidino, or piperidino group, which groups may be optionally substituted by one or 2 alkyl groups; and $R_3$ is alkyl, cycloalkyl, phenyl optionally substituted by fluorine or a group selected from

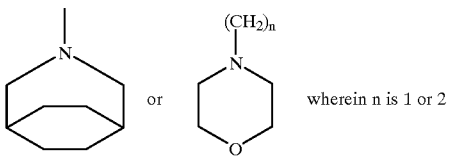

or wherein n is 1 or 2

Examples of particularly suitable compounds from within this class are those wherein X is hydrogen, and $R_1$ is methyl, $R_3$ is phenyl and $R_2$ is 3-methyl phenyl or 3-(5-oxo-1,2,4oxadiazol-3-yl) phenyl or $R_1$ is methyl, $R_2$ is 3-methyl phenyl and $R_3$ is

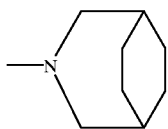

or $R_1$ is isopropyl, $R_3$ is phenyl and $R_2$ is 3-(1H-tetrazol-5-yl) phenyl.

or $R_1$ is $CH_2COR_4$ wherein $R_4$ is 2-methylphenyl, $R_2$ is 3 methylphenyl and $R_3$ is phenyl Further examples of suitable CCK-B antagonists for use in the invention include the 1,5-benzodiazepine derivatives having CCK-B antagonist activity described in WO9314074, WO9314075, WO94261491, WO9424151, WO9425444, WO9503299, WO9503284, WO9503285 and WO9425445.

The subject matter of the above identified patent applications is incorporated herein by reference.

Within the 1,5-benzodiazepine derivatives described in the above identified patent applications a particularly useful class of CCK-B antagonists for use in this invention are those of general formula (II).

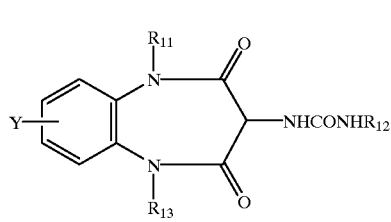

(II)

wherein $R_{11}$ represents a phenyl, $C_{3-7}$cycloalkyl, $C_{7-11}$ bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$ bridgedcycloalkyl group;

$R_{12}$ represents a phenyl group optionally substituted by 1 or 2 substituents selected from, halogen, $C_{1-4}$alkyl, $C_{1-4}$alkylthio, cyano, nitro, trifluoromethyl, trifluoromethoxy, $(CH_2)nR_{14}$ or $O(CH_2)pR_{14}$ wherein $R_{14}$ represents hydroxy, $C_{1-4}$alkoxy, $CO_2R_{15}$ or $NR_{16}R_{17}$; n is zero or 1; p is an integer from 1 to 4;

$R_{13}$ represents the group $AlkNR_{18}R_{19}$ or phenyl optionally substituted by 1 or 2 halogen atom;

$R_{15}$ represents hydrogen or $C_{1-4}$alkyl;

$R_{16}$ represents hydrogen or $C_{1-4}$alkyl;

$R_{17}$ represents hydrogen, $C_{1-4}$alkyl, acyl, or $C_{2-6}$alkyl substituted by one or more hydroxy, carboxyl and/or amino groups or $R_{16}$ and $R_{17}$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups.

$R_{18}$ and $R_{19}$ independently represent hydrogen, $C_{1-4}$alkyl or $C_{2-6}$alkyl substituted by one or more hydroxy, carboxyl and/or amino groups or $R_{18}$ and $R_{19}$ together with the nitrogen atom to which they are attached represent a 5–7 saturated heterocyclic ring which may contain an additional heteroatom selected from oxygen, sulphur or nitrogen and/or may be substituted by 1 or 2 $C_{1-4}$alkyl or hydroxy groups; Alk represents a straight or branched $C_{2-6}$alkylene chain optionally substituted by an hydroxyl group;

Y represents hydrogen or 1 or 2 halogen atoms;

and pharmaceutically acceptable salts and or metabolically labile esters.

For compounds of formula (II) examples of suitable $R_{11}$ groups include a $C_{4-6}$alkyl e.g. 3-methyl butyl, 3,3-dimethyl butyl, $C_{3-6}$ hydroxy alkyl e.g. 2-hydroxypropyl, 2-hydroxy-3- methylbutyl, 2-hydroxy-3,3-dimethylbutyl, $C_{1-2}$ alkyl substituted by a bridged $C_{7-10}$cycloalkyl group e.g. 2-norbornanylmethyl, 5-norbornenylmethyl, 1-adamantylmethyl, alkoxycarbonylalkyl, e.g. methoxycarbonylmethyl or t-butyoxycerbonylmethyl, cyclohexylmethyl, or 2-cyclopentylethyl.

Conveniently $R_1$ represents 3-methylbutyl or 1-adamantylmethyl and more particularly 1-adamantylmethyl.

When $R_{13}$ is an optionally substituted phenyl group this is conveniently phenyl or 2-fluorophenyl and more particularly phenyl.

When $R_{13}$ is the group $AlkNR_{18}R_{19}$; the group Alk conveniently represents ethylene, propylene or 2-hydroxymethyl-ethylene and more particularly ethylene.

Examples of suitable $NR_{18}R_{19}$ groups include amino, dimethylamino, diethylamino, morpholino, pyrrolidino, piperidino or hexamethyleneimino.

Conveniently $R_{13}$ represents morpholinoethyl, piperidinoethyl, pyrrolidinoethyl, dimethylaminoethyl, diethylaminoethyl, dimethylamino-propyl or 2-hydroxymethyl-2-aminoethyl or hexamethyleneiminoethyl. More preferably $R_{13}$ represents morpholinoethyl.

Y conveniently represents fluorine or chlorine or more particularly hydrogen.

A preferred group of compounds of formula (II) for use in the invention are those wherein $R_{11}$ represents 1-adamantylmethyl $R_{12}$ is phenyl optionally substituted in the meta position by a methyl, methoxy, methylthio, nitro, dimethylamino, ethoxycarbonyl or carbonyl group; $R_{13}$ is phenyl and Y is hydrogen. Within this group especially preferred compounds are those wherein $R_{12}$ is phenyl optionally substituted by dimethylamino, ethoxycarbonyl or carboxyl group.

A further preferred group of compounds of formula (II) for use in the present invention include those wherein $R_{11}$ is 1-adamantylmethyl, $R_{12}$ is phenyl optionally substituted by halogen e.g. fluorine or bromine, $R_{13}$ represents, 2-(4-morpholino)ethyl, 2-(1-piperidino)ethyl, 2-(1-pyrrolidino) ethyl, 2-(dimethylamino)ethyl, 3-(dimethylamino)propyl, 2-hydroxymethyl -2-aminoethyl, 3-aminopropyl, and Y is hydrogen or fluorine.

A yet further preferred group of compounds of formula (II) for use in the present invention include those wherein $R_{11}$ is 3-methylbutyl, $R_{12}$ is phenyl optionally substituted by methyl, methoxy, chlorine, bromine, fluorine, trifluoromethyl, hydroxy or methoxy, $R_{13}$ is 2-(dimethylamino)ethyl, 2diethylamino)ethyl, 2-(1-piperidino)ethyl or 2-(4-morpholino)ethyl, Y is hydrogen or fluorine.

A further preferred group of compounds of formula (II) are those wherein $R_{11}$ is 1-adamantylmethyl, $R_{13}$ is phenyl or the fluorophenyl and $R_{12}$ is phenyl or phenyl substituted by methyl, methoxy, methylthio, nitro, dimethylamino, ethoxycarbonyl or carboxy or $R_{13}$ represents 2-(4morpholino)ethyl, 2-(1-piperidino)ethyl, 2(1-pyrrolidino)ethyl, -2-dimethylamino)ethyl, 3-(dimethylamino)propyl, 2-hydroxymethyl -2-aminoethyl, 3-aminopropyl, $R_{12}$ is phenyl or phenyl substituted by methyl, methoxy or flourine, Y is hydrogen or fluorine, and more particularly hydrogen.

Specific preferred compounds of formula (II) for the treatment of sleep disorders include the specific preferred compounds described in WO9314074, WO9503285 and WO9503284.

Particularly preferred compounds of formula (II) for use in the treatment of sleep disorders include:
N-phenyl-N'-[2,3,4,5-tetrahydro-2,4-dioxo-1-(1-adamantylmethyl)-5-phenyl-1H-1,5-benzodiazepin-3-yl]urea;
N-[1-(1-Adamantylmethyl)-2,4dioxo-5-[2-4-morpholino)ethyl]-2,3,4,5-tetrahydro-1H-benzodiazepin-3-yl]-N'-phenylurea;
N-1[-(Adamantylmethyl)-2,4,-dioxo-5-phenyl-2,3,4,5-tetrahydro-1H-1,5-benzodiazepin-3-yl]-N'-(3carboxyphenyl)urea;
N-[(1-Adamantylmethyl)-5-[2-(dimethylamino)ethyl]-2,4-dioxo-2,3,4,5-tetrahydro-1H-1,5-benzodiazepin-3-yl]-N'-phenylurea;
and enantiomers and physiologically acceptable salts thereof.

It will be appreciated that compounds of formulae (I) and (11) possess at least one asymmetric carbon atom (namely the carbon atom occupying the 3-position of the diazepine ring) and the compounds of the invention thus include all stereoisomers and mixtures thereof including the racemates.

Further examples of CCK-B antagonists for use in the invention include the peptide derivatives described in EPA 4055537, WO 9204045, WO 9204322, WO9204348 WO 9113907 and EPA all of which by way of reference are incorporated herein.

Conveniently the peptide derivatives with CCK-B antagonist activity for use in the invention include the tryptophan based dipeptoids and in particular;
[1S-[1α,2β,[S*(S*)],4α]-4-[[2-[[3-(1H-3-yl)-2-methyl-1-1-oxo-2-[[[(1,7,7-trimethylbicyclo[2.2.1 ]hept-2-yl)oxy]carbonyl]amino]propyl]amino-1-phenylethyl]amino]-4-oxobutanoic acid and salts thereof and
(R-(R*,R*))-4-((2-((3-(1H-indol-3-yl)-2-methyl-2-(((tricyclo(3.3.1.1,3,7)dec-2-yloxy)carbonyl)amino)propyl)amino) -1-phenylethyl)amino)-4-oxobutanoic acid and salts thereof.

Yet further examples of CCK-B agonists for use in the treatment of sleep disorders include those described in WO9507261, WO9503281, EP620221, WO9419322, WO9400421, WO9401421, WO9315059, WO9321172, EP518731, WO9210479, USP53997308, EP655053, WO9505359, WO9419322, WO9406802, WO9426718, WO9294045 and EP46714.

From within the compounds described therein particularly useful compounds include the 3-phenylureido-azepin-2-ones and 3-phenylureido-benzazepin-2-ones described in WO9315059 and which are incorporated herein by way of reference. From within this class a particularly interesting compound is N-tert butyl 2[3-[3-(3-chlorophenyl)ureido)-2-oxo-5-phenyl-4,3,4,5-tetrahydro-1H-(1)-benzazepin-1-yr]ethanoic acid amide.

A further interesting class CCK-8 antagonist for use in the invention are the aspartic acid and glutamic acid derivatives described in WO9210479 and WO9507261. Examples of particularly suitable compounds from within this class are spiroglumide and related compounds.

Preferred CCK-B antagonist for use in the treatment of sleep disorders include.
(a) 1,4-benzodiazepines of formula (I) and more particularly the compounds wherein X is hydrogen, $R_1$ is methyl, $R_2$ is 3-methylphenyl or 3-(5 oxo-1,2,4-oxadiazol-3-yl) phenyl and $R_3$ is phenyl; X is hydrogen. $R_1$ is methyl, $R_2$ is 3 methylphenyl and $R_3$ is 3-azabicyclo-3.3.1]nonan-3-yl, X is hydrogen, $R_1$ is $CH_2COR$ wherein $R_4$ is 2-methylphenyl, $R_2$ is 3methylphenyl and $R_3$ is phenyl or X is hydrogen, $R_1$ is isopropyl, $R_3$ is phenyl and $R_2$ is 3 (1H -tetrazol-5-yl) phenyl.
(b) 1,5 benzadiazepines of formula (II) and more particularly the compounds.
N-phenyl-N'-[2,3,4, 5-tetrahydro-2,4-dioxo-1-(adamantylmethyl)-5-phenyl-1H-1,5-benzodiazepin-3-yl]urea;
N[1-(1-Adamantylmethyl)-2,4dioxo-5-[2-(4-morpholino)ethyl]-2,3,4,5-tetrahydro-1H-benzodiazepin-3-yl]-N'-phenylurea;
N-1[-(Adamantylmethyl)-2,4,-dioxo-5-phenyl-2,3,4,5-tetrahydro-1H-1,5-benzodiazepin-3-yl]-N'-(3carboxyphenyl)urea;
N-[(1-Adamantylmethyl)-5-[2-(dimethylamino)ethyl]-2,4-dioxo-2,3,4,5-tetrahydro-1H-1,5-benzodiazepin-3-yl]-N'-phenylurea;
(c) the tryptophan peptide derivatives.
[1S-[1α,2β,[S*(S*)],4α]-4-[[2-[[3-(1H-3-yl)-2-methyl1-1-oxo-2-[[[(1,7,7-trimethylbicyclo[2.2.1]hept-2-yl)oxy]carbonyl]amino]propyl]amino]-1-phenylethyl]amino]-4-oxobutanoic acid and salts thereof and
(R-(R*,R*))-4-((2-((3-(1H-indol-3-yl)-2-methyl-2-(((tricyclo(3.3.1.1,3,7)dec-2-yloxy)carbonyl)amino) propyl) amino)-1-phenylethyl)amino)4-oxobutanoic acid and salts thereof;
(d) N-tert butyl-2-[3[3-(3chlorophenyl)ureido-2-oxo-5-phenyl-2,3,4,5 tetrahydro-1H-(1)-benzazepin-1-yl]ethanoic acid amide.
(e) (R)-γ(3,5dichloro-benzamido]δ-oxo-8-azaspiro[4,5]decane8-valeric acid (spiroglumide).

References hereinafter to a CCK-8 antagonists (I) also includes where appropriate pharmaceutically acceptable salts and or solvates thereof.

Particularly useful CCK-B antagonists for use in the treatment of sleep disorders are:
(+) N-phenyl-N'-[2,3,4,5-tetrahydro-2,4-dioxo-1-(1-adamantylmethyl)-5-phenyl-1H-1,5-benzodiazepin-3-yl]urea (compound 1);
(−) N-[1-(1-Adamantylmethyl)-2,4-dioxo-5-[2-(4-morpholino)ethyl]-2,3,4,5-tetrahydro-1H-benzodiazepin-3-yl]-N'-phenylurea (compound 2);
N-(2,3-dihydro-1-methyl-2-oxo-5-phenyl-1H-1,4-benzodiazepin-3-yl]-N'-3-methylphenyl urea (compound 3);
(R-(R*, R*))4-((2-((3-(1H-indol-3-yl)-2-methyl-2-((tricyclo (3,3,1,1,3,7)dec-2yloxy)carbonyl)amino propyl)amino)-1-phenylethyl)amino-4-oxo-butanoic acid meglumine salt (compound 4).
N-1[-(Adamantylmethyl)-2,4,-dioxo-5-phenyl-2,3,4,5-tetrahydro-1H-1,5-benzodiazepin-3-yl]-N'-(3-carboxyphenyl)urea (compound 5);

N-[(1-Adamantylmethyl)-5-[2-dimethylamino)ethyl]-2,4-dioxo-2,3,4,5-tetrahydro-1H-1,5-benzodiazepin-3-yl]-N'-phenylurea (compound 6);

The ability of the compounds which exhibit CCK-B antagonist activity to influence sleep patterns may be demonstrated by examining EEG parameters in old rats. In these animals the EEG patterns are disturbed. Administration of an effective amount of a CCK-B antagonist to such an animal alters the EEG pattern towards the normal. These effects may be observed using standard procedures such as those described by H.Depoortere et al. Physiology & Behaviour 1993, 54, 785–793.

Thus CCK-B antagonists may be useful for the treatment of sleep disorders, including Disorders of Initiating and Maintaining Sleep (insomnias), (DIMS) which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbance as seen in ageing. Disorders of the Sleep-Wake Schedule which include jet-lag, disorder due to shift work, delayed sleep phase syndrome, advanced sleep phase syndrome, non-24 h sleep phase syndrome, disorders due to blindness and those caused by ageing and dementias. Dysfunctions associated with sleep (parasomnias) for example sleep related enuresis.

According to a further aspect of the invention we provide a method for the treatment of mammal, including man, for sleep disorders which method comprises administering an effective amount of a CCK-B antagonist or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of the CCK-B antagonist required for use in treatment will vary with the nature of the condition being treated and the age and the condition of the patient and will be ultimately at the discretion of the attendant physician. In general however doses employed for adult human treatment will typically be in the range of 0.01–2000 mg per day e.g 0.01–500 mg per day.

The desired dose may conveniently be presented in a single dose or as divided doses administered at appropriate intervals, for example as two, three, four or more sub-doses per day.

While it is possible that, for use in therapy, the CCK-B antagonist may be administered as the raw chemical it is preferable to present the active ingredient as a pharmaceutical formulation.

The invention thus further provides a pharmaceutical formulation for the treatment of sleep disorders comprising a CCK-B antagonist or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acic. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form which may be obtained by freeze drying for constitution with a suitable vehicle, e.g. sterile, pyrogen-free water, before use.

The composition according to the invention may also be formulated as a depot preparation Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt The compositions according to the invention may contain between 0.1–99% of the active ingredient, conveniently from 30–95% for tablets and capsules and 3–50% for liquid preparations.

Examples of suitable pharmaceutical formulations for use in the treatment of sleep disorders include those already specifically described in the specifications of the patent applications referred to above and incorporated hereinto by reference.

For administration in the form of a tablet a convenient formulation is as follows:

| Ingredient | mg/tab |
| --- | --- |
| CCK-B antagonist | 1.00 |
| Povidone K-30 | 0.11 |
| Microcrystalline Cellulose | 142.44 |
| Croscarmellose sodium | 6.00 |

| Ingredient | mg/tab |
| --- | --- |
| Magnesium Stearate | 0.45 |
| Compression weight | 150.00 mg |

The CCK-B antagonist and Povidone are dissolved in a suitable solvent such as a mixture of acetone and methanol and the resultant solution spray dried using conventional equipment. The resulting powder is blended with the remaining excipients and compressed using 7.5 mm normal concave looking. The tablets are coated using conventional methods and equipment. An example of a suitable coating material is Opadry white OY-S-7322 (Colorcon). The above formulation is particularly convenient for use with the CCK-B antagonist—Compound 1.

PHARMACOLOGICAL ACTIVITY

The ability of CCK-B antagonists to effect sleep patterns in old rats was measured by examining the effect of the compound on the EEG pattern using the procedures described by H Depoortere et al. Physiology & Behaviour 1993 54, 785–793. In this test it was found that a single dose i.p. or p.o. of the CCK-B antagonist resulted in an improvement in total sleep time, in both NREM and REM together with being less awake and with a shorter awakening duration. Thus doses of compounds 1 to 6 identified above that resulted in a significant improvement in total sleep time pattern are as follows:

| CCK-B Antagonist | Dose |
| --- | --- |
| Compound 1 | 5 μg/kg ip and po |
| Compound 2 | 0.5 μg/kg ip |
| Compound 3 | 5 μg/kg ip |
| Compound 4 | 5 μg/kg ip |
| Compound 5 | 15 μg/kg ip |
| Compound 6 | 0.5 μg/kg ip |

What is claimed is:

1. A method for the treatment for sleep disorders which comprises administering an effective amount of a CCK-B antagonist or a pharmaceutically acceptable salt thereof to the patient wherein the CCK-B receptor antagonist is selected from the group consisting of a 1,4-benzodiazepine derivative, a 1,5-benzodiazepine derivative, a peptide derivative, a 3-phenylureido-azepen-2-one, a 3-phenylureido-benzazepin-2-one derivative, an aspartic acid derivative and a glutamic acid derivative.

2. A method according to claim 1, wherein the CCK-B receptor antagonist is a 1,4 benzodiazepine derivative of formula (I)

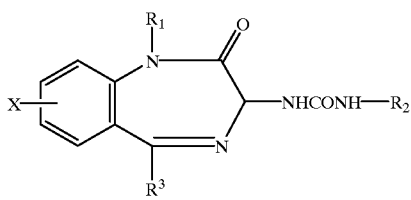

(I)

and N-oxides thereof and pharmaceutically acceptable salts thereof wherein
$R_1$ represents $C_{1-6}$ alkyl (optionally substituted by hydroxyl $C_{1-4}$ alkoxy, $COR_4$, $CONR_5R_6$ or $C_{3-7}$ cycloalkyl) or $C_{3-7}$ cycloalkyl;
$R_4$ represents $C_{1-6}$ alkoxy or optionally substituted phenyl;
$R_5$ is methyl or ethyl and $R_6$ is phenyl or $R_5$ and $R_6$ together form a $C_4$–$C_6$ alkylene chain, which may be substitued by 1 or 2 alkyl groups;
$R_2$ represents a substituted or unsubstituted phenyl group (wherein the substitutents may be 1 or 2 of halo, $C_{1-4}$ alkyl, nitro, cyano, trifluoromethyl, trifluoromethoxy, $C_{1-4}$alkylthio or $(CH_2)n R_7$ wherein $R_7$ is hydroxy, $C_{1-4}$ alkoxy, $CO_2R_8$, $NR_8R_9$, $SO_2NR_8COR_{10}$, $CONR_8SO_2R_{10}$, or $R_7$ represents a tetrazolyl, carboxamidotetrazolyl, 3-trifluoromethyl-1,2,4-triazolyl or 5-oxo-1,2,4 oxadiazolyl group, which groups may be substituted on one of the nitrogen atoms by a $C_{1-4}$alkyl group;
$R_8$ represents hydrogen of a $C_{1-4}$alkyl group;
$R_9$ independently represents hydrogen or a $C_{1-4}$alkyl group or the group $SO_2CF_3$;
$R_{10}$ represents $C_{1-4}$alkyl;
$R_3$ represents $C_{1-6}$ alkyl, $C_{3-7}$ cycloalkyl, phenyl (optionally substituted by halogen), azacycloalkyl or alkyl substituted by an amino, $C_{1-4}$ alkylamino, $diC_{1-4}$alkylamino, morpholino, pyrrolidino, piperidino, hexamethylene, thiomorpholino or N-methyl piperazino group; X represents hydrogen or halogen.

3. A method according to claim 1, wherein the CCK-B antagonist is a 1,4-benzodiazepine derivative of formula (I) wherein X is hydrogen, $R_1$ is methyl, $R_2$ is 3-methylphenyl or 3-(5 oxo-1,2,4-oxadiazol-3-yl) phenyl and $R_3$ is phenyl; X is hydrogen, $R_1$ is methyl, $R_2$ is 3 methylphenyl and $R_3$ is 3-azabicyclo-[3.3.1]nonan-3-yl, X is hydrogen, R1 is $CH_2COR_4$ wherein $R_4$ is 2-methylphenyl, $R_2$ is 3-methylphenyl and $R_3$ is phenyl or X is hydrogen, $R_1$ is isopropyl, $R_3$ is phenyl and $R_2$ is 3 (1-tetrazol-5-yl) phenyl.

4. A method according to claim 1, wherein the CCK-B antagonists is a 1,5 benzodiazepine derivative of formula (II)

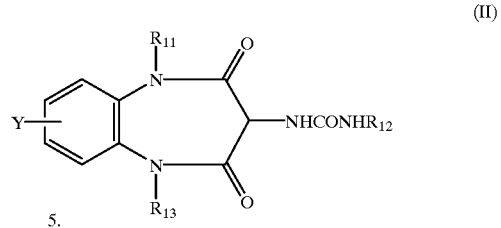

(II)

wherein
$R_{11}$ represents a phenyl, $C_{3-7}$cycloalkyl, $C_{7-11}$ bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$ bridgedcycloalkyl group;
$R_{12}$ represents a phenyl group optionally substituted by 1 or 2 substituents selected from, halogen, $C_{1-4}$alkyl, $C_{1-4}$alkylthio, cyano, nitro, trifluoromethyl, trifluoromethoxy, $(CH_2)nR_{14}$ or $O(CH_2)pR_{14}$ wherein $R_{14}$ represents hydroxy, $C_{1-4}$alkoxy, $CO_2R_{15}$ or $NR_{16}R_{17}$; n is zero or 1; p is an integer from 1 to 4;
$R_{13}$ represents the group $AlkNR_{18}R_{19}$ or phenyl optionally substituted by 1 or 2 halogen atom;
$R_{15}$ represents hydrogen or $C_{1-4}$alkyl;

$R_{16}$ represents hydrogen or $C_{1-4}$alkyl;

$R_{17}$ represents hydrogen, $C_{1-4}$alkyl, acyl, or $C_{2-6}$alkyl substituted by one or more hydroxy, carboxyl and/or amino groups or $R_{16}$ and $R_{17}$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups;

$R_{18}$ and $R_{19}$ independently represent hydrogen, $C_{1-4}$alkyl or $C_{2-6}$alkyl substituted by one or more hydroxy, carboxyl and/or amino groups or $R_{18}$ and $R_{19}$ together with the nitrogen atom to which they are attached represent a 5–7 saturated heterocyclic ring which may contain an additional heteroatom selected from oxygen, sulphur or nitrogen and/or may be substituted by 1 or 2 $C_{1-4}$alkyl or hydroxy groups; Alk represents a straight or branched $C_{2-6}$alkylene chain optionally substituted by an hydroxyl group;

Y represents hydrogen or 1 or 2 halogen atoms;

and pharmaceutically acceptable salts and or metabolically labile esters.

5. A method according to claim 4 wherein the CCK-B antagonist is a compound selected from:

N-phenyl-N'-[2,3,4,5-tetrahydro-2,4-dioxo-1-(1-adamantylmethyl)-5-phenyl-1H-1,5-benzodiazepin-3-yl] urea;

N-[1-(1-Adamantylmethyl)-2,4-dioxo-5-[2-(4-morpholino) ethyl]-2,3,4,5-tetrahydro-1H-benzodiazepin-3-yl]-N'-phenylurea;

N-1[-(Adamantylmethyl)-2,4,-dioxo-5-phenyl-2,3,4,5-tetrahydro-1H-1,5-benzodiazepin-3-yl]-N'-(3-carboxyphenyl)urea;

N-[(1-Adamantylmethyl)-5-[2-(dimethylamino)ethyl]-2,4-dioxo-2,3,4,5-tetrahydro-1H-1,5-benzodiazepin-3-yl]-N'-phenylurea;

and enantiomers thereof.

6. A method according to claim 1, wherein the CCK antagonists is a peptide derivative selected from

[1S-[1α,2β,[S*(S*)],4α]-4-[[2-[[3-(1H-3-yl)-2-methyl1-1-oxo-2-[[[(1,7,7-trimethylbicyclo[2.2.1]hept-2-yl)oxy] carbonyl]amino]propyl]amino]-1-phenylethyl]-amino]4-oxobutanoic acid and salts thereof and (R-(R*,R*)-4-((2-((3-(1H-indol-3-yl)-2-methyl-2-(((tricyclo(3.3.1.1,3,7)dec-2-yloxy)carbonyl)amino) propyl)amino)-1-phenylethyl)amino)-4-oxobutanoic acid and salts thereof.

7. A method according to claim 1, or wherein the CCK-B antagonist is N-tert butyl-2-[3[3-(3-chlorophenyl)ureido-2-oxo-5-phenyl-2,3,4,5 tetrahydro-1H-(1)-benzazepin-1-yl] ethanoic acid amide.

8. A method according to claim 1, wherein the CCK-B antagonist is (R)-γ(3,5-dichloro-benzamido]δ-oxo-8-azaspiro[4,5]decane-8-valeric acid.

9. A method according to claim 1 wherein the CCK-B antagonist is (+) N-phenyl-N'-[2,3,4,5-tetrahydro-2,4-dioxo-1-(1-adamantylmethyl)-5-phenyl-1H-1,5-benzodiazepin-3-yl]urea.

10. A method according to claim 1 wherein the CCK-B antagonist is (−) N-[1-(1-Adamantylmethyl)-2,4-dioxo-5-[2-(4-morpholino)ethyl]-2,3,4,5-tetrahydro-1H-benzodiazepin-3-yl]-N'-phenylurea;

N-(2,3-dihydro-1-methyl-2-oxo-5-phenyl-1H-1,4-benzodiazepin-3-yl]-N'-3-methylphenyl urea;

(R-(R*,R*))4-((2-((3-(1H-indol-3-yl)-2-methyl-2-((tricyclo (3,3,1,1,3,7)dec-2-yloxy)carbonyl)aminopropyl)amino)-1-phenylethyl)amino-4-oxobutanoic acid meglumine salt;

N-1[-(Adamantylmethyl)-2,4,-dioxo-5-phenyl-2,3,4,5-tetrahydro-1H-1,5-benzodiazepin-3-yl]-N'-(3-carboxyphenyl)urea; or N-[(1-Adamantylmethyl)-5-[2-dimethylamino)ethyl]-2,4-dioxo-2,3,4,5-tetrahydro-1H-1,5-benzodiazepin-3-yl]-N'-phenylurea.

11. A method for the treatment for sleep disorders according to claim 1, wherein the peptide derivative is a tryptophan based dipeptoid.

12. A method for the treatment of sleep disorders in accordance with claim 1, which moves nonrapid eye movement and rapid eye movement sleep to a normal balance.

* * * * *